United States Patent
Shima et al.

(10) Patent No.: US 6,908,879 B1
(45) Date of Patent: Jun. 21, 2005

(54) CERAMIC ARTICLE, CARRIER FOR CATALYST, METHODS FOR PRODUCTION THEREOF, CATALYST FOR PRODUCING ETHYLENE OXIDE USING THE CARRIER, AND METHOD FOR PRODUCING ETHYLENE OXIDE

(75) Inventors: Masahide Shima, Kawasaki (JP); Hitoshi Takada, Yokohama (JP)

(73) Assignee: Nippon Shokubai Co., Ltd., Osaka (JP)

( * ) Notice: Subject to any disclaimer, the term of this patent is extended or adjusted under 35 U.S.C. 154(b) by 709 days.

(21) Appl. No.: 09/654,674

(22) Filed: Sep. 5, 2000

(30) Foreign Application Priority Data

Sep. 6, 1999 (JP) .......................... 11-251883
Nov. 24, 1999 (JP) .......................... 11-332588

(51) Int. Cl.[7] ................ B01J 21/08; B01J 21/12; B01J 21/14; B01J 23/00; B01J 20/00
(52) U.S. Cl. ............... 502/242; 502/263; 502/351; 502/355; 502/407; 502/414; 502/415; 502/439; 501/73; 501/133; 501/134; 501/153; 501/154; 423/327.1; 423/335; 423/598; 423/600
(58) Field of Search ............... 502/242, 263, 502/351, 355, 407, 414, 415, 439, 251; 501/73, 133, 134, 153, 154; 423/327.1, 398, 335, 598, 600; 428/65.6

(56) References Cited

U.S. PATENT DOCUMENTS

| | | | | |
|---|---|---|---|---|
| 4,316,965 A | * | 2/1982 | Oda et al. ............ | 501/112 |
| 4,483,944 A | | 11/1984 | Day et al. ............ | 502/439 |
| 4,631,267 A | * | 12/1986 | Lachman et al. ...... | 502/439 |
| 4,631,269 A | * | 12/1986 | Lachman et al. ...... | 502/439 |
| 4,764,498 A | * | 8/1988 | Wissner et al. ...... | 502/251 |
| 4,812,437 A | | 3/1989 | Nojiri et al. ......... | 502/243 |
| 5,004,709 A | * | 4/1991 | Stranford et al. ..... | 501/97 |
| 5,077,256 A | | 12/1991 | Yamamoto et al. .... | 502/243 |
| 5,100,859 A | | 3/1992 | Gerdes et al. ........ | 502/439 |
| 5,316,996 A | * | 5/1994 | Itoh ................... | 502/238 |
| 5,322,821 A | * | 6/1994 | Brezny ................ | 501/80 |
| 5,395,812 A | | 3/1995 | Nagase et al. ........ | 502/238 |
| 5,512,530 A | * | 4/1996 | Gerdes et al. ........ | 502/351 |
| 5,633,081 A | * | 5/1997 | Clough et al. ........ | 428/331 |
| 5,645,619 A | * | 7/1997 | Erickson et al. ...... | 51/309 |
| 5,669,941 A | * | 9/1997 | Peterson ............. | 51/295 |
| 5,733,840 A | * | 3/1998 | Szymanski et al. .... | 502/351 |
| 5,733,842 A | * | 3/1998 | Gerdes et al. ........ | 502/439 |
| 6,117,814 A | * | 9/2000 | Plecha et al. ........ | 502/325 |
| 6,329,315 B1 | * | 12/2001 | Denton et al. ........ | 502/232 |

FOREIGN PATENT DOCUMENTS

| | | | |
|---|---|---|---|
| EP | 0 174 851 A1 | 3/1986 | ............ C03C/3/04 |
| EP | 0 207 550 B1 | 9/1990 | ............ B01J/23/66 |
| GB | 1 602 777 | 11/1981 | ............ B01J/21/12 |
| JP | 54-32408 | 3/1979 | ............ C07D/303/04 |
| JP | 55-145677 | 11/1980 | ............ C07D/301/10 |
| JP | 62-4444 | 1/1987 | ............ B01J/23/66 |
| JP | 63-116743 | 5/1988 | ............ B01J/23/66 |
| JP | 2-194839 | 8/1990 | ............ B01J/23/66 |
| JP | 5-329368 | 12/1993 | ............ B01J/23/66 |
| JP | 6-47278 | 2/1994 | ............ B01J/23/02 |
| WO | WO 97/46317 | 12/1997 | ............ B01J/23/66 |
| WO | WO 99/39825 | 8/1999 | ............ B01J/21/08 |

OTHER PUBLICATIONS

Tanabe et al., "Acid Base Catalysts", Sangyo Tosho K.K. 160–163 and 176, Apr. 28, 1996, English Translation.

\* cited by examiner

*Primary Examiner*—Cam N. Nguyen
(74) *Attorney, Agent, or Firm*—Fish & Richardson P.C.

(57) ABSTRACT

A ceramic article is disclosed which contains aluminum, silicon, and titanium in a total amount of at least 99% by weight as reduced to the oxides ($Al_2O_3+SiO_2+TiO_2$) and assumes an acidic color in methyl red, an indicator of at least pKa+4.8. It can be used as a carried for a catalyst. This ceramic article is obtained by mixing an aluminum compound, a silicon compound, and a titanium compound and calcining the resultant mixture at a temperature in the range of 1,000°–2,000° C. A catalyst for preparing ethylene oxide is obtained by depositing silver and a reaction promoter on the ceramic carrier and ethylene oxide is obtained by oxidizing ethylene with a molecular oxygen-containing gas in the presence of the catalyst in vapor phase.

6 Claims, No Drawings

CERAMIC ARTICLE, CARRIER FOR CATALYST, METHODS FOR PRODUCTION THEREOF, CATALYST FOR PRODUCING ETHYLENE OXIDE USING THE CARRIER, AND METHOD FOR PRODUCING ETHYLENE OXIDE

BACKGROUND OF THE INVENTION

1. Field of the Invention

This invention relates to a novel ceramic article, a carrier for a catalyst, methods for the production thereof, a catalyst for producing ethylene oxide using the carrier, and method for producing ethylene oxide. Particularly, it relates to a ceramic article calcined at elevated temperatures and endowed with acid points, a carrier for use in a catalyst, methods for the production thereof, a catalyst for producing ethylene oxide using the carrier, and method for producing ethylene oxide. More particularly, it relates to a ceramic article containing aluminum, silicon, and titanium and manifesting strong acid points in consequence of the calcining at 1,000°–2,000° C., a carrier for use in a catalyst, methods for the production thereof, and method for producing ethylene oxide.

2. Description of the Prior Art

The ceramic articles using the oxides of aluminum, silicon, titanium, etc. as basic materials generally possess exceptionally excellent thermal, mechanical, electrical, and chemical properties and find utility in applications too many to enumerate. Those of the ceramic articles which excel in thermal and mechanical strength are extensively utilized in the field of chemical industry as a carrier for a catalyst and as a refining material and in the field of bioceramics as artificial bones and artificial teeth which are required to possess affinity for living organism. Those of the ceramic articles which possess chemical properties are used for analysis utilizing the adsorbing desorbing property of a chemical substance and particularly those of the ceramic articles which possess acid points are utilized by themselves as a catalyst for the oxidation of olefins and the dehydrogenation of hydrated compounds.

JP-A-54-32,408, for example, discloses a non-acidic filler containing alumina, silica, and titania in a total amount of not less than 99% by weight, containing metals of the groups Va, VIa, VIIa, VIII, Ib, and IIb in the Periodic Table of the Elements in a total amount of less than 0.1% by eight as reduced to metal oxides, and assuming no acidic color in methyl red having a pKa of +4.8.

Further, JP-A-55-145,677 discloses a method for the production of ethylene oxide characterized by using a silver catalyst formed by using the non- acidic filler mentioned above as a catalyst carrier and depositing thereon silver and, when necessary, further an alkali metal component or an alkaline earth metal component. U.S. Pat. No. 4,812,437 discloses a carrier composed mainly of α-alumina and having a specific surface area, water absorption ratio, average pore diameter, silica content and sodium content and assuming acidic color in an indicator having pKa of +4.8.

JP-A-62-4,444 discloses that a carrier having small amount of impurities is obtained by mixing an aluminum compound with a salt of a metal of the group IA in the Periodic Table of the Elements and calcining it, and the catalyst using the carrier is excellent in stability. JP-A-4-363,139 discloses a carrier which contains an element of 4–6 Cycles of the groups IIIa–VIIa and IIIb–Vb in the Periodic Table of the Elements in α-alumina and the catalyst using such carrier gives high selectivity and long life. Further, U.S. Pat. No. 5,100,859 discloses a carrier comprising a high purity α-alumina, an alkali earth metal oxide, a silicon oxide and zirconium oxide, and the catalyst using such catalyst gives a high initial selectivity and long life.

On the other hand, a carrier for a catalyst provided on the surface of α-alumina with a coating layer of amorphous silica and used for the production of ethylene oxide (U.S. Pat. No. 5,077,256) and a carrier for a catalyst provided on the surface of α-alumina with a coating layer of amorphous silica-alumina and used for the production of ethylene oxide (U.S. Pat. No. 5,395,812) have been known to the art. These patent publications, however, neither suggest anything about a ceramic article containing aluminum, silicon, and titanium and manifesting acidity nor propose anything about a method for the production of the ceramic article.

Generally, ceramic articles possessing acid points are used as a dynamic blade and static blade of a gas turbine and a combustion chamber of a reciproengine as a construction material, for spraying on a turbine blade or a corn as a thermal isulation material and for a thermal absorption material utilizing the acidity thereof, but as a chemical use there are used as catalysts or carriers for use in catalysts which are useful for various oxidation reactions, reduction reactions, addition reactions, and decomposition reactions. They are required to possess high thermal stability in any of these applications and they derive huge economic effects from the high thermal stability. It is predicted that a high-temperature heat treatment will suffice to impart high thermal stability and mechanical strength to such carriers. It is also the fact that the heat treatment performed at a high temperature deprives the such carriers of acid points.

An object of this invention, therefore, is to provide a novel ceramic article, a carrier for a catalyst, methods for the production thereof, a catalyst for producing ethylene oxide using the carrier, and method for producing ethylene oxide.

Another object of this invention is to provide a ceramic article calcined at a high temperature and endowed with high thermal stability and acid points, a carrier for a catalyst, method for the production thereof, a catalyst for producing ethylene oxide using the carrier, and method for producing ethylene oxide.

Still another object of this invention is to provide a catalyst for producing ethylene oxide excellent in a catalyst performance, i.e., activity, selectivity and life, and a method for producing ethylene oxide using such catalyst.

SUMMARY OF THE INVENTION

These objects are accomplished by the following times (1)–(22).

(1) A ceramic article containing aluminum, silicon, and titanium in a total amount of at least 99% by weight as reduced to the oxides ($Al_2O_3+SiO_2+TiO_2$) and assuming an acidic color in methyl red, an indicator of pKa+4.8.

(2) A ceramic article set forth in (1) above, wherein the aluminum content is in the range of 70.0–99.5% by weight calculated as $Al_2O_3$, the silicon content is in the range of 0.06–12% by weight calculated as $SiO_2$ and the titanium content is in the range of 0.08–30% by weight calculated as $TiO_2$.

(3) A method for the production of a ceramic article containing aluminum, silicon, and titanium in a total amount of at least 99% by weight as reduced to the oxides ($Al_2O_3+SiO_2+TiO_2$) and assuming an acidic color in methyl red, an indicator of pKa+4.8, which comprises calcining a mixture containing an aluminum compound, a silicon compound, and a titanium compound at a temperature in the range of 1,000°–2,000° C.

(4) A method set forth in (3) above, wherein the aluminum content in the ceramic is in the range of 70.0–99.5% by weight calculated as $Al_2O_3$, the silicon content is in the range of 0.06–12% by weight calculated as $SiO_2$ and the titanium content in the range of 0.08–30% by weight calculated as $TiO_2$ in the ceramic.

(5) A method set forth in (3) or (4) above, wherein said aluminum compound is α-alumina.

(6) A method set forth in any of (3)–(5) above, wherein the silicon compound and the titanium compound are compounds which are capable of forming an amorphous layer of silica and titania by being calcined together.

(7) A method set forth in (5) above, wherein the α-alumina has an alumina crystal diameter in the range of 0.1–5 μm, a particle diameter in the range of 50–100 μm, and a BET specific surface area in the range of 0.1–4 $m^2/g$.

(8) A carrier for a catalyst formed of a shaped article of a ceramics containing aluminum, silicon, and titanium in a total amount of at least 99% by weight as reduced to the oxides ($Al_2O_3+SiO_2+TiO_2$) and assuming an acidic color in methyl red, an indicator of pKa+4.8.

(9) A carrier set forth in (10) above, wherein the aluminum content is in the range of 70.0–99.5% by weight, calculated as $Al_2O_3$, the silicon content is in the range of 0.06–12% by weight calculated as $SiO_2$ and the titanium content is in the range of 0.08–30% by weight calculated as $TiO_2$.

(10) A carrier set forth in any of (8) or (9) above, wherein the shaped article is in the form of spheres, pellets, or rings.

(11) A method for the production of a carrier for a catalyst containing aluminum, silicon, and titanium in a total amount of at least 99% by weight as reduced to the oxides ($Al_2O_3+SiO_2+TiO_2$) and assuming an acidic color in methyl red, an indicator of pKa+4.8, which method comprises forming a mixture containing an aluminum compound, a silicon compound, and a titanium compound in a shape and then calcining the shaped mixture at a temperature in the range of 1,000°–2,000° C.

(12) A method set forth in (11) above, wherein the aluminum content in the ceramic is in the range of 70.0–99.5% by weight calculated as $Al_2O_3$, the silicon content is in the range of 0.06–12% by weight calculated as $SiO_2$ and the titanium content in the range of 0.08–30% by weight in the ceramic.

(13) A method set forth in (11) or (12) above, wherein the aluminum compound is α-alumina.

(14) A method set forth in any of (11)–(13), above, wherein the silicon compound and said titanium compound are compounds which are capable of forming an amorphous layer of silica and titania by being calcined together.

(15) A method set forth in (13) above, wherein the α-alumina has an alumina crystal diameter in the range of 0.1–5 μm, a particle diameter in the range of 50–100 μm, and a BET specific surface area in the range of 0.1–4 $m^2/g$.

(16) A catalyst for producing ethylene oxide which comprises depositing a silvent component and at least one element selected from the group consisting an alkali metal and an alkali earth metal in a carrier set forth in any one of (8)–(10) above.

(17) A catalyst set forth in (16) above, wherein the alkali metal is cesium.

(18) A method for preparing a catalyst of production of ethylene oxide which comprises depositing a silver component and a reaction promoter component on the carrier set forth in any one of (8)–(10) above, calcining it in oxidative atmosphere at a temperature of 150°–450° C. for 0.1–10 hours, and then calcining it in a reducing atmosphere at a temperature of 450°–800° C. for 0.1–10 hours.

(19) A method for producing ethylene oxide which comprises oxiding ethylene by a molecular oxygen-containing gas in the presence of the catalyst set forth in (16) or (17) above in vapor phase.

Since the ceramic article according to this invention possesses high thermal stability and storing acid points, the shaped article thereof is useful as a catalyst or a carrier for a catalysts as in oxidation reactions, reduction reactions, addition reactions, and decomposition reactions and excellent in service life and performance in high-temperature reactions as well. Further, the catalyst for producing ethylene oxide obtained by using the carrier in accordance with the present invention is excellent in catalyst performance, especially in selectivity.

EXPLANATION OF THE PREFERRED EMBODIMENT

The ceramic article according to this invention is obtained, as described above, by calcining a mixture containing an aluminum compound, a silicon compound, and a titanium compound at a temperature in the range of 1,000°–2,000° C.

As typical examples of the aluminum compound to be used in this invention, α-alumina, β-alumina, and γ-alumina may be cited. Among other aluminum compounds cited above, α-alumina proves particularly advantageous. The α-alumina itself does not need to be particularly restricted. It may be any of such compounds as are generally used as α-alumina. It is particularly preferred to have an alkali metal content in the range of 1–70 m.mols, especially in the range of 2–30 m.mols, per kg thereof (expressed in this invention as 1–70 m.mols/kg (α-alumina powder). When the finished product suffers alumina to be present therein in an amount of not less than 99.5% by weight, it manifest acid points with difficult. Properly, the aluminum content in the finished product is in the range of 70.0–99.5% by weight, preferably 80.0–99.0% by weight, and more preferably in the range of 90.0–98.5% by weight.

To be used effectively in this invention, the α-alumina possesses an alumina crystal diameter (average primary particle diameter) in the range of 0.1–5 μm, preferably 0.5–4 μm, a particle diameter (average secondary particle diameter) in the range of 30–100 μm, preferably 50–80 μm, further a BET specific surface area in the range of 0.1–4 $m^2/g$, preferably 0.5–3.0 $m^2/g$, and moreover a coefficient of linear contraction by two hours' calcination at 1,700° C. in the range of 12–20%. The expression "coefficient of linear contraction by two hours' calcination at 1,700° C." as used herein means the coefficient of linear contraction which is obtained when a sample resulting from pulverizing α-alumina to the size of α-crystals (primary particles), shaping the sample under a pressure of 1 ton/$cm^2$, and calcining the shaped article at 1,700° C. for two hours.

The ceramic article of this invention contains aluminum, silicon and titanium in a total amount of at least 99% by weight as reduced to the oxides ($Al_2O_3+SiO_2+TiO_2$), preferably at least 99.5% by weight. It is obtained, for example, by mixing α-alumina having the aforementioned low alkali metal content with a titanium compound and a silicon compound together with an organic binding agent and a pore forming agent which are normally used and calcining the resultant mixture at a temperature in the range of 1,000°–2,000° C. This calcination operation is believed to form an amorphous silica-titania coating layer on the outer surface of α-alumina and on the inner surface of pores thereof.

One of the characteristics of this invention resides in the formation of such an amorphous silica-titania coating layer on the surface of the α-alumina and the consequent manifestation of strong acid points apparently originating in the coating layer. The acid strength can be readily determined by a method which is described from page 161 onward in "Acid-Base Catalysts" written jointly by Kozo Tanabe and Tsuneichi Takeshita and published by Sangyo Tosho K.K. on Apr. 26, 1966. The ceramic article of this invention contains aluminum, silicon, and titanium, has a total content of alumina ($Al_2O_3$), silica ($SiO_2$), and titania ($TiO_2$) of at least 99% by weight, and assumes a color in methyl red as an indicator of pKa+4.8. Further, by controlling the composition and the conditions of preparation of the ceramic article, it is made possible to manufacture an alumina-silica-titania type ceramic article which assumes a color in phenyl azo naphthylamine, an indicator of pKa+4.0, p-dimethyl aminoazobenzene, an indicator of pHa+3.3, 2-amino-5-azo toluene, an indicator of pKa+2.0, or even dicinnamal acetone, an indicator of pKa–3.0. This alumina-silica-titania type ceramic article is expected to find utility in various applications, depending on the acid strength and the amount of acid. Particularly it is possible to prepare a carrier which has strong acid points and assumes a color at pKa+2.0 or –3.0 proves and the carrier having these properties is suitable for a catalyst intended for the production of ethylene oxide.

As the titanium compound mentioned above, any of the titanium compounds can be used so long as it is capable of forming an amorphous silica-titania layer by being calcined together with a silicon compound which will be described more specially below. As typical examples of the titanium compound, titanium hydrate and titanium oxides (anatase, rutile, and amorphous form) may be cited. These titanium compounds may be used either singly or in the form of two or more members. They may be used in the form of synthesized products or natural produces. The titanium compound does not need to be particularly discriminated on account of the state of aggregate. It may be incorporated in the mixture in any arbitrary state such as, for example, powder, sol, or aqueous solution. When the titanium compound is in the state of powder, it properly has a particle diameter in the range of 1–300 nm, preferably in the range of 1–20 nm. Among other titanium compounds, colloidal titania having a particle diameter in the range of 1–300 nm, preferably 1–20 nm, is used particularly advantageously. From the viewpoint of the ease of dispersion, this colloidal titania is preferred to be used in the form of titania sol. This titania sol can be obtained, for example, by a method which comprises hydrolyzing titanium salt or a method which comprises neutralizing an aqueous titanium salt solution with an alkali thereby forming a gel provisionally and then peptizing the gel.

The silicon compound mentioned above to be effectively used herein is only required to be capable of forming an amorphous silica-titania by being calcined together with an aluminum compound and a titanium compound. As typical examples of the silicon compound, silica, feldspar, clay, silicon nitride, silicon carbide, silane, and silicates may be cited. Besides, such aluminosilicates as silica-alumina and mullite are also usable. These silicon compounds may be used either singly or in the form of two or more members. They may be used in the form of synthesized products or natural produces. The silicon compound does not need to be particularly discriminated on account of the state of aggregate. It may be incorporated in the mixture in any arbitrary state such as, for example, powder, sol, or aqueous solution. When the silicon compound is in the state of powder, it properly has a particle diameter in the range of 1–300 nm, preferably in the range of 1–20 nm. Among other silicon compounds, colloidal silica having a particle diameter in the range of 1–300 nm, preferably 1–20 nm, is used particularly advantageously. Due to high dispersibility, this colloidal silica is preferred to be used in the form of an aqueous solution. This colloidal silica can be obtained, for example, by a method which comprises neutralizing an aqueous sodium silicate solution with an acid thereby forming a gel provisionally and then peptizing the gel or a method which comprises depriving an aqueous sodium silicate solution of sodium by means of ion exchange.

As the organic binding agent mentioned above, any of organic biding agents which are generally used in the preparation of any ordinary ceramic article, especially carrier can be used. As typical examples of the organic binding agent, gum arabic, polyvinyl, alcohol, hydroxyethyl cellulose, methyl cellulose, carboxymethyl cellulose, and corn starch may be cited. Among other organic binding agents mentioned above, methyl cellulose and corn starch can be used particularly advantageously in respect that they produce ashes only in a small amount after the step of calcination.

The silicon content in the novel ceramic article or carrier of this invention is in the range of 0.06–12% by weight calculated as $SiO_2$ of the ceramic article or carrier. The silicon content in the ceramic article or the carrier is preferably in the range of 0.6–6% by weight, more preferably in the range of 1.2–3% by weight.

Total amount of the aluminum, silicon and titanium calculated as $Al_2O_3$, $SiO_2$ and $TiO_2$ is at least 99% by weight.

The titanium content is in the range of 0.08–30% by weight calculated as $TiO_2$ of the ceramic article or carrier. The titanium content in the ceramic article or carrier is preferred to be in the range of 0.8–25% by weight, more preferably in the range of 1.6–16% by weight.

The silicon content and the titanium content in the ceramic article or carrier can be calculated from the results of the fluorescent X-ray diffraction analysis of the ceramic article for composition.

The amounts of the aluminum compound, silicon compound, and titanium compound to be used in the prepared of the novel ceramic article of this invention may be properly decided so that the contents of aluminum, silicon, and titanium in the produced ceramic article may fall in the respective ranges specified above. Preferably, the Ti/Si ratio is in the range of 0.005–20, preferably 0.5–10, and more preferably 3–6. The amount of the organic binding agent to be used does not need to be particularly restricted but may be properly selected to suit the purpose of use optimally.

The method for preparing the novel ceramic article of this invention does not need to be particularly discriminated. For example, the preparation may be attained by mixing an aluminum compound, a silicon compound, a titanium compound, and an organic binding agent, molding the resultant mixture, and then calcining the molded mixture at a temperature in the range of 1,000°–2,000° C. To be specific, the method comprises adding a silicon compound, a titanium compound, and an organic binding agent to α-alumina, optionally further adding water thereto, and thoroughly mixing them by the use of a mixing device such as a kneader, then extrusion molding the resultant mixture, granulating the molded mixture, drying the granules, and calcining the dry granules at a temperature in the range of 1,000°–2,000° C., preferably 1,200°–1,700° C., and more preferably 1,300°–1,600° C. Though the extrusion molding may be effected in a dry form or a wet form, it is generally carried out in a wet form. The drying operation mentioned above is generally carried out at a temperature in the range of 80°–900° C. It may be omitted as occasion demands.

The organic binding agent may be used in conjunction with a pore forming agent such as, for example, a powder obtained by pulverizing shells and seeds of peaches, apricots, and walnuts to a uniform particle diameter or a substance having a uniform particle diameter and possessing the ability to disappear when calcined.

The ceramic article of this invention on account of the chemical property of its own is advantageously used as a catalyst or a carrier for a catalyst. When it is used as a catalyst or a carrier for a catalyst, it does not need to be particularly limited in shape. Generally, it is used in such a granular form as spheres, pellets, and rings. As regards the size thereof, it has an average equivalent diameter generally in the range of 3–20 mm, preferably 5–10 mm.

Specifically, from the ceramic article mentioned above, a carrier for a catalyst is obtained by molding the ceramic article in the shape mentioned above prior to the step of calcination and calcining the produced formed article under the conditions mentioned above. The carrier thus obtained is advantageously used particularly for a silver catalyst having deposited thereon silver and an alkali metal oxide and used for the production of ethylene oxide by the oxidation of ethylene with a molecular oxygen-containing gas.

The specific surface area of the carrier contemplated by this invention is generally in the range of 0.03–10 $m^2/g$, preferably 0.1–5 $m^2/g$, and more preferably 0.3–2 $m^2/g$. If the specific surface area is unduly small, the shortage will be at a disadvantage in suffering the sinter to proceed excessively and preventing impartation of a satisfactory coefficient of water absorption to the carrier and rendering deposition of a catalyst component on the carrier difficult. Conversely, if the specific surface area is unduly large, the excess will be at a disadvantage in decreasing the pore diameter and accelerating the sequential oxidation of the produced ethylene oxide. The coefficient of water absorption is generally in the range of 10–70%, preferably 20–60%, and more preferably 30–50%. If the coefficient of water absorption is unduly low, the shortage will be at a disadvantage in rendering deposition of a catalyst component difficult. Conversely, if it is unduly high, the excess will be at a disadvantage in disabling acquisition of a satisfactory crushing strength. The average pore diameter is generally in the range of 0.1–5 μm, preferably 0.2–3 μm, and more preferably 0.3–0.9 μm. If the average pore diameter is unduly large, the excess will be at a disadvantage in degrading the activity. Conversely, it is unduly small, the shortage will be at a disadvantage in inducing stagnation of gas and promoting the sequential oxidation of the produced ethylene oxide. The porosity is generally in the range of 40–80% and preferably 50–70%. If the porosity is unduly low, the shortage will be at a disadvantage in enlarging the specific gravity of the carrier excessively. If it is unduly high, the excess will be at a disadvantage in preventing the carrier from acquiring satisfactory crushing strength.

The catalyst for producing ethylene oxide in accordance with the present invention can be prepared by a general method which is used in the catalyst for producing ethylene oxide except the above-mentioned carrier. The catalyst component deposited on the carrier may be silver solely or combination of silver and a reaction promoter such as cesium. The "depositions of a silver component" of the present invention is depositions of silver in addition of the embodiment the deposition of silver and a reaction promoter.

Typically, for example, a silver compound solely for forming silver, the silver compound, a complexing agent for forming a silver complex or further an aqueous solution containing the reaction promoter if necessary is prepared, after impregnating it with the carrier, it is dried and calcined. Drying is preferably carried out in air, oxygen gas or an inert gas atmosphere such as nitrogen gas at a temperature of 80°–120° C. Calcination is preferably carried out in air, oxygen gas or an inert gas atmosphere at a temperature of 150°–800° C. Further, the calcinations may be carried out in one step or two steps or more. Among them, it is preferable that the first step is carried out in anoxidizing atmosphere such as air at a temperature of 150°–250° C. for 0.1–10 hours and the second step is carried out in an oxidizing atmosphere such as air at a temperature of 250°–450° C. for 0.1–10 hours. Further the third step is preferably carried out in an inert gas atmosphere selected form the group consisting of nitrogen, helium and argon at a temperature of 450°–800° C. for 0.1–10 hours.

Typical examples of the above-mentioned silver compound, silver nitrate, silver carbonate, silver oxalate, silver acetate, silver propionate, silver lactate, silver citrate, silver neodecanate, etc. can be cited. As the typical example of complexing agent, monoethanol-amine, diethanolamine, triethanolamine, ethylenediamine, propylenediamine, etc. can be cited. As the typical reaction promoter, alkali metal such as lithium, sodium, potassium, rubidium and cesium, thalium, sulfur, chromium, molybdenum, tungsten, etc. can be cited. These can be used solely or a combination of two combination or more.

As the catalyst for preparing ethylene oxide in accordance with the present invention, the catalyst deposited silver and a reaction promoter as the catalyst component is preferable. As the reaction promoter, an oxide of an alkali metal such as sodium, potassium, cesium, etc., and an oxide of an alkali earth metal such as barium, calcium, magnesium, etc. can be cited, and among them the alkali metal, especially cesium is preferable. An amount of silver to be deposited is generally 1–30% by weight of catalyst, preferably 5–20% by weight of catalyst. An amount of the reaction promoter to deposited is generally 0.001–1% by weight of catalyst, preferably 0.01–0.5% by weight of catalyst, more preferably 0.1–0.3% by weight of catalyst.

Ethylene oxide can be obtained by oxidizing ethylene by a molecular oxygen-containing gas in the presence of the catalyst thus obtained in vapor phase.

The standard conditions which prevail in the production on a commercial scale, namely a reaction temperature in the range of 180°–300° C., preferably 200°–260° C., a reaction pressure in the range of 0.2–4 MPa, preferably 1.5–4 MPa, and a space velocity in the range of 1,000–30,000 $hr^{-1}$ (STP), preferably 3,000–8,000 $hr^{-1}$ (STP). As respects the composition of the feed gas which is passed through the catalyst, the method of using 0.5–40% by volume of ethylene, 3–10% by volume of oxygen, 5–30% by volume of carbon dioxide gas, and the balance of such an inert gas as, for example, nitrogen, or argon, and further using steam and a lower hydrocarbon such as methane or ethane and, as a reaction inhibitor, 0.1–10 ppm (by volume) of an organic chloride compound such as ethylene dichloride, ethyl chloride or vinyl chloride can be suitably adopted.

As typical examples of the molecular oxygen-containing gas to be used in this invention, air, oxygen, and enriched air may be cited.

Now, this invention will be described more specifically below with reference to working examples.

EXAMPLE 1

In a kneader, 89.5 parts by weight of α-alumina powder (A) (average alumina crystal diameter: 1 μm, average particle diameter: 65 μm, BET specific surface area: 2.2 m$^2$/g, coefficient of linear contraction by calcining at 1,700° C. for 2 hours: 15%, and sodium content: 16 m.mol/kg), 0.5 part by weight of silica sol having an average particle diameter in the range of 2–20 nm (as reduced to $SiO_2$) (made by Nissan Chemicals Industries, Ltd. and sold under the trademark designation of "Snowtex-O"), 10 parts by weight of titania powder (made by Wako Pure Chemical Industries, Ltd.), 6 parts by weight of methyl cellulose, 6 parts by weight of corn starch, and 30 parts by weight walnut shells (100–170 μm) were thoroughly mixed and the resultant mixture was further mixed with 40 parts by weight of water added thereto. The produced mixture was extrusion molded, to a ring shape, dried, and calcined at 1500° C. for 2 hours to afford a ceramic article (A).

This ceramic article (A) was found to have a silicon content of 0.5% by weight calculated as $SiO_2$ and a titanium content of 10% by weight calculated as $TiO_2$. The total composition of the ceramic article was found to be 99.9% by weight as reduced to $Al_2O_3+SiO_2+TiO_2$. It was found to have an average equivalent diameter of 8 mm, a BET specific surface area of 1.1 m$^2$/g, a coefficient of water absorption of 41%, an average pore diameter of 0.7 μm, and a porosity of 61%. By acid strength measurement, it showed acid color in an indicator of pKa +4.8, an indicator of pKa +4.0, an indicator of pKa +3.3 and an indicator of pKa +2.0. This is referred to a carrier (A) hereinafter.

The carrier (A) thus obtained was washed with boiling water three times and dried. 210 g of the washed carrier was impregnated with a complex solution containing 57.3 g of silver oxalate, 38.6 ml of monoethanolamine, 41.4 ml of water and 0.22 g of cesium nitrate, and then heated, concentrated, further dried at a temperature of 120° C. for 40 minutes, and heated in air stream at a temperature of 170° C. for 30 minute and at a temperature of 270° C. for 30 minutes to obtain a catalyst (a) for preparing ethylene oxide.

EXAMPLE 2

In a kneader, 93 parts by weight of the same α-alumina powder (A) as used in Example 1, 1 part by weight (as reduced to $SiO_2$) of the same silica sol as used in Example 1, 6 parts by weight of titania powder, 6 parts by weight of methyl cellulose, and 6 parts by weight of corn starch were thoroughly mixed and the resultant mixture was further mixed with 40 parts by weight of water. The produced mixture was extrusion molded, granulated, dried, and calcined at 1,400° C. for 2 hours to afford a ceramic article (B). This ceramic article (B) was found to have a silicon content of 1% by weight calculated as $SiO_2$, a titanium content of 6% by weight calculated as $TiO_2$, and a total composition of 99.9% by weight as reduced to $Al_2O_3+SiO_2+TiO_2$. It was found to have an average equivalent diameter of 8 mm, a BET specific surface area of 1.6 m$^2$/g, a coefficient of water absorption of 45%, an average pore diameter of 0.8 μm, and a porosity of 64%.

By acid strength measurement, it showed acid color in an indicator of pKa +4.8, an indicator of pKa +4.0, an indicator of pKa +3.3 and an indicator of pKa +2.0. This is referred to a carrier (B) hereinafter.

A catalyst (b) for preparing ethylene oxide was obtained by the same method of Example 1 except that the carrier (B) was used.

EXAMPLE 3

In a kneader, 95 parts by weight of the same α-alumina powder A as used in Example 1, 4 parts by weight (as reduced to $SiO_2$) of the same silica sol as used in Example 1 parts by weight of titania powder, 6 parts by weight of methyl cellulose, and 6 parts by weight of corn starch were thoroughly mixed and the resultant mixture was further mixed with 40 parts by weight of water. The produced mixture was extrusion molded, granulated, dried, and calcined at 1,550° C. for 2 hours to afford a ceramic article (C). This ceramic article (C) was found to have a silicon content of 4% by weight calculated as $SiO_2$, a titanium content of 1% by weight calculated as $TiO_2$, and a total composition of 99.9% by weight as reduced to $Al_2O_3+TiO_2$. It was found to have an average equivalent diameter of 8 mm, a BET specific surface area of 0.7 m$^2$/g, a coefficient of water absorption of 38%, an average pore diameter of 0.6 μm, and a porosity of 58%.

By acid strength measurement, it showed acid color in an indicator of pKa +4.8, an indicator of pKa +4.0, an indicator of pKa +3.3 and an indicator of pKa +2.0. This is referred to a carrier (C) hereinafter.

A catalyst (c) for preparing ethylene oxide was obtained by the same method of Example 1 except that the carrier (C) was used.

EXAMPLE 4

In a kneader, 93 parts of by weight of α-alumina powder (B) (average alumina crystal diameter: 1 μm, average particle diameter: 65 μm, BET specific surface area: 0.9 m$^2$/g, coefficient of linear contraction by calcining at 1,700° C. for 2 hours: 15%, and sodium content: 16 m.mols/kg), 1 part by weight of silica sol (as reduced to $SiO_2$), 4 parts by weight of titania powder, 6 parts by weight of methyl cellulose and, 6 parts by weight of corn starch were thoroughly mixed and the resultant mixtures was further mixed with 40 parts by weight of water added thereto. The produced mixture was extrusion molded, granulated, dried, and calcined at 1600° C. for two hours to afford a ceramic article (D).

This ceramic article (D) was found to have a silicon content of 1% by weight calculated as $SiO_2$ and a titanium content of 4% by weight calculated as $TiO_2$. The total composition of the ceramic article was found to be 99.9% by weight as reduced to $Al_2O_3+SiO_2+TiO_2$. It was found to have an average equivalent diameter of 8 mm, a BET specific surface area of 0.6 m$^2$/g, a coefficient of water absorption of 34%, an average pore diameter of 0.5 μm, and a porosity of 56%. By acid strength measurement, it showed acid color in an indicator of pKa +4.8, and indicator of pKa +4.0, an indicator of pKa +3.3 and an indicator of pKa +2.0. This is referred to a carrier (D) hereinafter.

The carrier (D) thus obtained was washed with boiling water three times and dried, 210 g of the washed carrier was impregnated with a complex solution containing 57.3 g of silver oxalate, 38.8 ml of monoethanolamine, 41.4 ml of water and 0.81 g of cesium nitrate, and then heated, concentrated, further dried at a temperature of 120° C. for 40 minutes, and heated in air stream at a temperature of 170° C. for 30 minute and at a temperature of 270° C. for 30 minute, and furthermore calcined in nitrogen stream at a temperature of 650° C. for 2 hours to obtain a catalyst (d) for preparing ethylene oxide.

Control 1

In a kneader, 99.6 parts by weight of the same α-alumina powder A as used in Example 1, 0.4 part by weight (calculated as $TiO_2$) of the same titania powder as used in Example 1, 6 parts by weight of methyl cellulose, and 6 parts by weight of corn starch were thoroughly mixed and the resultant mixture was further mixed with 40 parts by weight of water added thereto. The produced mixture was extrusion molded, granulated, dried, and calcined at 1,200° C. for two hours to afford a ceramic article (E).

By acid strength measurement, it did not show acid color in an indicator of pKa +4.8, an indicator of pKa +4.0, an indicator of pKa +3.3 and an indicator of pKa +2.0. This is referred to a carrier (E) hereinafter.

A catalyst (e) for preparing ethylene oxide was obtained by the same method of Example 1 except that the carrier (E) was used.

Control 2

In a kneader, 97.5 parts by weight of the same α-alumina powder A as used in Example 1, 1 part by weight (calculated as $TiO_2$) of the same titania powder as used in Example 1, and 12 parts by weight of carboxymethyl cellulose (8% by weight calculated as $Na_2O$) were thoroughly mixed and the resultant mixture was further mixed with 40 parts by weight of water added thereto. The produced mixture was extrusion molded, granulated, dried, and calcined at 1,100° C. for two hours to afford a ceramic article (F).

By acid strength measurement, it did not show acid color in an indicator of pKa +4.8, an indicator of pKa +4.0, an indicator of pKa +3.3 and an indicator of pKa +2.0. This is referred to a carrier (F) hereinafter.

A catalyst (f) for preparing ethylene oxide was obtained by the same method of Example 1 except that the carrier (F) was used.

Control 3

In a kneader, 99.9 parts by weight of an α-alumina powder (C) (average alumina crystal particle: 3.0 μm, average particle diameter: 100 μm, BET specific surface area: 0.7 $m^2/g$, coefficient of linear contraction by calcining at 1,700° C. for two hours: 13%, and sodium content: 90 m.mols/kg), 0.1 part by weight (as reduced to $SiO_2$) of the same silica sol as used in Example 1, 6 parts by weight of methyl cellulose, and 6 parts by weight of corn starch were thoroughly mixed and the resultant mixture was further mixed with 40 parts by weight of water added thereto. The produced mixture was extrusion molded, granulated, dried, and calcined at 1,700° C. for two hours to afford a ceramic article (G). This ceramic article (G) was found to have an average equivalent diameter of 8 mm, a BET specific surface area of 1.0 $m^2/g$, a coefficient of water absorption of 32%, an average pore diameter of 0.6 μm, and a porosity of 55%.

By acid strength measurement, it did not show acid color in an indicator of pKa +4.8, an indicator of pKa +4.0, an indicator of pKa +3.3 and an indicator of pKa +2.0. This is referred to carrier (G) hereinafter.

A catalyst (g) for preparing ethylene oxide was obtained by the same method of Example 1 except that the carrier (G) was used.

EXAMPLE 5

The carriers (A)–(G) were tested for acid strength in accordance with the method which is described from page 161 onward in "Acid-Base Catalysts" written jointly by Kozo Tanabe and Tsuneichi Takeshita and published by Sangyo Tosho K. K. on Apr. 26, 1966. The samples used in the test were each prepared by boiling to clean a given calcined ceramic article in 10 times its own weight of purified water for 30 minutes, repeating this boiling treatment twice, then drying the cleaned ceramic article at 120° C. for 18 hours, allowing the hot dried article to cool to normal room temperature, classifying the cooled ceramic article into sizes of 100–200 meshes, weighing a 0.1-g portion of the separated powder in a sample vial, and drying the portion in the vial at 120° C. for five hours. The results of the test are shown in Table 1.

TABLE 1

| Carrier | Acid strength (pKa) | | | | | | |
|---|---|---|---|---|---|---|---|
| | +7.2 | +4.8 | +4.0 | +3.3 | +2.0 | −3.0 | −5.6 |
| (A) | ++ | ++ | ++ | ++ | + | + | − |
| (B) | ++ | ++ | ++ | ++ | + | + | − |
| (C) | ++ | ++ | ++ | ++ | + | + | − |
| (D) | ++ | ++ | ++ | ++ | + | + | − |
| (E) | ++ | − | − | − | − | − | − |
| (F) | ++ | − | − | − | − | − | − |
| (G) | ++ | − | − | − | − | − | − |

EXAMPLE 6

The catalysts (a)–(g) were each pulverized and classified in sizes of 600–850 μm. The reaction tubes of stainless steel measuring 3 mm in inside diameter and 600 mm in length were respectively packed with the consequently produced powders, 1.2 g in weight, and used for gas phase oxidation of ethylene under the following conditions. When the degree of conversion of ethylene reached 10%, the selectivity for ethylene oxide and the reaction temperature of the catalyst bed were measured. The results are shown in Table 2.

<Reaction conditions>

Space velocity: 6150 $hr^{-1}$

Reaction pressure: 2.1 Mpa Composition of raw material gas: Ethylene 20%, oxygen 7.6%, carbon dioxide 5.7%, ethylene dichloride 2.2 ppm, (methane, nitrogen, argon, and ethane) balance

TABLE 2

| Catalyst used | Selectivity (%) | Reaction temperature (° C.) |
|---|---|---|
| a | 81.2 | 234 |
| b | 81.4 | 233 |
| c | 81.2 | 234 |
| d | 81.4 | 234 |
| e | 79.5 | 246 |
| f | 79.3 | 248 |
| g | 79.5 | 250 |

The entire disclosure of Japanese Patent Application No. 11-251883 filed on Sep. 6, 1999 and No. 11-332588 filed on Nov. 24, 1999 including specification, claims and summary are incorporated therein by reference in its entirely.

What is claimed is:

1. A ceramic article containing aluminum, silicon, and titanium in a total amount of at least 99% by weight as reduced to the oxides ($Al_2O_3+SiO_2+TiO_2$), wherein the aluminum content is in the range of 70.0–99.5% by weight calculated as $Al_2O_3$ the silicon content is the range of 0.06–12% by weight calculated as $SiO_2$ and the titanium content is in the range of 0.08–30% by weight calculated as $TiO_2$, and the acid strength of the ceramic article is such that when it is exposed to methyl red indicator of pKa +4.8, the methyl red indicator changes color to its acid color.

2. A method for the production of a ceramic article containing aluminum, silicon, and titanium in a total amount of at least 99% by weight as reduced to the oxides ($Al_2O_3$+$SiO_2$+$TiO_2$) comprising calcining admixture containing an aluminum compound, a silicon compound, and a titanium compound at a temperature in the range of 1,000° C.–2,000° C., wherein, the acid strength of the ceramic article is such that when it is exposed to a methyl red indicator of pKa +4.8, the methyl red indicator changes color to its acid color.

3. A method according to claim 2, wherein the aluminum content in said ceramic article is in the range of 70.0–99.5% by weight calculated as $Al_2O_3$, the silicon content in said ceramic article is in the range of 0.06–12% by weight calculated as $SiO_2$ and the titanium content in the range of 0.08–30% by weight calculated as $TiO_2$ in said ceramic article.

4. A method according to claim 2, wherein said aluminum compound is α-alumina.

5. A method according to claim 4, wherein said α-aluminum has an alumina crystal diameter in the range of 0.1–5 μm, a particle diameter in the range of 50–100 μm, and a BET specific surface area in the range of 0.1–4 $m^2$/g.

6. A method according to claim 2, wherein said silicon compound and said titanium compound are capable of forming an amorphous layer of silica and titania by being calcined together.

* * * * *